US011160975B2

(12) United States Patent
Mercanzini et al.

(10) Patent No.: US 11,160,975 B2
(45) Date of Patent: Nov. 2, 2021

(54) APPARATUS FOR STIMULATION OF AUTONOMIC NERVOUS SYSTEM

(71) Applicant: ALEVA NEUROTHERAPEUTICS, Lausanne (CH)

(72) Inventors: Andre Mercanzini, Saint Sulpice (CH); Zbynek Struzka, Lausanne (CH); Jason Jinyu Ruan, Lausanne (CH)

(73) Assignee: ALEVA NEUROTHERAPEUTICS, Lausanne (CH)

( * ) Notice: Subject to any disclaimer, the term of this patent is extended or adjusted under 35 U.S.C. 154(b) by 99 days.

(21) Appl. No.: 16/289,406

(22) Filed: Feb. 28, 2019

(65) Prior Publication Data

US 2019/0269907 A1 Sep. 5, 2019

Related U.S. Application Data

(60) Provisional application No. 62/637,717, filed on Mar. 2, 2018.

(51) Int. Cl.
*A61N 1/36* (2006.01)
*A61N 1/05* (2006.01)
*A61B 5/00* (2006.01)
*A61B 5/24* (2021.01)

(52) U.S. Cl.
CPC ........ *A61N 1/0556* (2013.01); *A61N 1/36117* (2013.01); *A61B 5/24* (2021.01); *A61B 5/4035* (2013.01); *A61B 2562/028* (2013.01); *A61B 2562/164* (2013.01); *A61N 1/36053* (2013.01)

(58) Field of Classification Search
CPC .............. A61N 1/0556; A61N 1/36117; A61N 1/36053; A61B 5/04001; A61B 5/4035; A61B 2652/028; A61B 2562/164; A61B 5/24

See application file for complete search history.

(56) References Cited

U.S. PATENT DOCUMENTS

| | | | | |
|---|---|---|---|---|
| 5,466,247 A | * | 11/1995 | Scheiner | A61N 1/05 600/377 |
| 2003/0040785 A1 | * | 2/2003 | Maschino | A61N 1/0556 607/118 |
| 2008/0065209 A1 | * | 3/2008 | Pflueger | A61F 5/566 623/9 |
| 2008/0177366 A1 | * | 7/2008 | Bolea | A61N 1/36185 607/118 |
| 2013/0303923 A1 | * | 11/2013 | Lerner | A61B 5/02208 600/492 |
| 2015/0174396 A1 | * | 6/2015 | Fisher | A61B 5/04001 600/377 |
| 2016/0128767 A1 | * | 5/2016 | Azamian | A61B 18/1492 606/41 |
| 2018/0117312 A1 | * | 5/2018 | Schmidt | A61N 1/0556 |

* cited by examiner

*Primary Examiner* — Ankit D Tejani
*Assistant Examiner* — Joshua Brendon Solomon
(74) *Attorney, Agent, or Firm* — Foley & Lardner LLP

(57) ABSTRACT

The present disclosure discusses a nerve cuff that includes a thin-film elastic mesh with an integrated array of electrodes. The nerve cuff can wrap around a human carotid artery or other tissue to stimulate the autonomic nervous system. The nerve cuff can include a housing that secures the mesh to the carotid artery or other tissue.

20 Claims, 12 Drawing Sheets

APPARATUS FOR STIMULATION OF AUTONOMIC NERVOUS SYSTEM

CROSS-REFERENCE TO RELATED APPLICATIONS

The present application claims the benefit, under 35 USC § 119(e), of the filing of U.S. Provisional Patent Application 62/637,717 filed Mar. 2, 2018. This provisional application is incorporated herein by reference for all purposes.

BACKGROUND

The autonomic nervous system can regulate fundamental bodily functions, such as breathing, heartbeat, and digestive processes. The stimulation of the autonomic nervous system can pose various challenges for a chronically implantable stimulation apparatus.

SUMMARY

The present disclosure describes a nerve cuff. The nerve cuff can include a microelectromechanical system (MEMS) elastic mesh film. The mesh film can include an integrated array of electrodes. The nerve cuff can be highly compliant to adapt to the expansions and contractions of the tissue to which the nerve cuff is coupled. The mesh film can include a plurality of openings to facilitate the expansion and the contraction of the mesh film without applying detrimental pressure to the tissue.

The mesh film can include an array of electrodes. The electrodes can be individually addressable to enable the selective simulation of different portions of tissue passing through the nerve cuff. The individually addressable electrodes also enable therapeutic stimulations to be delivered through the electrodes making a relatively strong electrical connection with the tissue and not the electrodes making a relatively weak electrical connection with the tissue.

According to at least one aspect of the disclosure, an implantable cuff can include a housing to at least partially enclose around a target tissue. The housing can include a first side plate and a second side plate coupled with the first side plate at a hinge. The cuff can include a mesh film. The mesh film can include a first panel coupled with an inner face of the first side plate. The first panel can include a first plurality of electrodes. The mesh film can include a second panel coupled with an inner face of the second side plate. The second panel can include a second plurality of electrodes. The mesh film can include a bridge coupling the first panel with the second panel.

The housing can include a first plurality of holes defined through the first side plate to enable at least one of a gas flow or a fluid flow through the first side plate. The housing can include a second plurality of holes defined through the second side plate to enable at least one of the gas flow or the fluid flow through the second side plate. The mesh film can include a first plurality of openings defined through the first panel and a second plurality of openings defined through second first panel.

The cuff can include a tether extending from the first panel. The tether can include a plurality of contacts. The tether can include a plurality of contacts and a plurality of traces. Each of the plurality of traces can couple one of the plurality of contacts to at least one first plurality of electrodes or second plurality of electrodes. The tether can include a plurality of contacts and a plurality of traces. Each of the plurality of traces can couple one of the plurality of contacts to at least one first plurality of electrodes or second plurality of electrodes. The first side plate and the second side plate can include a medical-grade silicone. The target tissue can be a carotid artery. The mesh film can include at least one metal layer defining the first plurality of electrodes and the second plurality of electrodes. The mesh film can include at least one barrier layer that at least partially encapsulates the at least one metal layer. The target tissue can be one of a hypoglossal nerve, a vagus nerve, a carotid artery bundle, a carotid artery bundle, or a glossopharyngeal nerve.

According to at least one aspect of the disclosure, a method can include forming a film. The film can include a first panel that can include a first plurality of electrodes. The film can include a second panel that can include a second plurality of electrodes. The film can include a bridge coupling the first panel with the second panel. The method can include forming a housing that can include a first side plate and a second side plate coupled with the first side plate at a hinge. The method can include coupling the first panel of the film with an inner face of the first side plate and the second panel of the film with an inner face of the second side plate.

The method can include forming a first plurality of holes through the first side plate to enable at least one of a gas flow or a fluid flow through the first side plate and forming a second plurality of holes through the second side plate to enable at least one of the gas flow or the fluid flow through the second side plate. The method can include defining a first plurality of openings through the first panel and defining a second plurality of openings through second first panel.

The method can include forming a tether extending from the first panel. The tether can include a plurality of contacts. The tether can include a plurality of contacts and a plurality of traces. Each of the plurality of traces can couple one of the plurality of contacts to at least one first plurality of electrodes or second plurality of electrodes. The tether can include a plurality of traces where each of the plurality of traces couple one of the plurality of contacts to at least one first plurality of electrodes or second plurality of electrodes.

The method can include forming the first side plate and the second side plate by injection molding a medical-grade silicone. The method can include etching at least one metal layer defining the first plurality of electrodes and the second plurality of electrodes. The method can include at least partially encapsulating the at least on metal layer with at least one barrier layer. The method can include coupling the film with the housing with an epoxy. The method can include deforming at least one of the first side plate and the second side plate to define an opening between the first side plate and the second side plate.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure describes a nerve cuff with a MEMS elastic mesh film. The mesh film can include an integrated array of electrodes. The nerve cuff is configured to wrap around a target site. For example, the nerve cuff can wrap around a carotid artery to stimulate the autonomic nervous system.

The carotid arteries, such as the internal or external carotid artery, are in proximity to various nerve branches that can modulate the autonomic nervous system with some nerve branches lying directly on the artery. The nerve cuff can surround the artery to stimulate the nerves lying directly on the artery (and other nerves).

The nerve cuff of the present disclosure can make secure, electrical contact with the carotid artery (and other tissue), but is compliant to enable expansion and contraction with the expansion and contraction of the carotid artery. Additionally, the nerve cuff's electrode array can enable the selective simulation of nerves that can be distributed over the surface of the artery or other target site.

Figure 1:
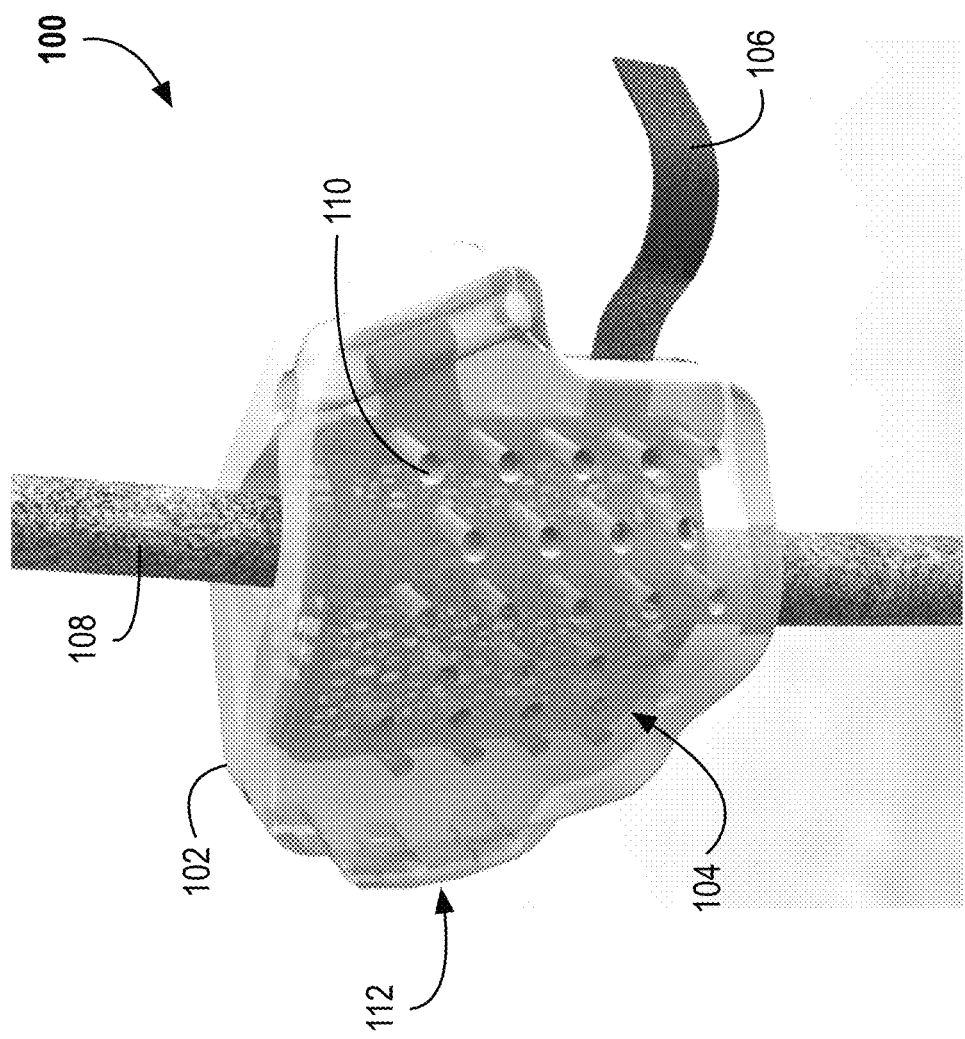
FIG. 1 illustrates an example nerve cuff coupled with an artery.

FIG. 1 illustrates an example nerve cuff 100. The nerve cuff 100 is coupled around an artery 108. The nerve cuff 100 can be coupled around or with other target tissue, such as the vagus nerve. The nerve cuff 100 includes a housing 102. A mesh film 104 is positioned on an inside face of the housing 102. The mesh film 104 can also be referred to as a film 104. A portion of the mesh film 104 can make contact with the artery 108 (or other target tissue). The mesh film 104 includes a tether 106. The housing 102 is further described in relation to FIGS. 2-6, among others. The mesh film 104 is further described in relation to FIGS. 7-11, among others.

Figure 2:
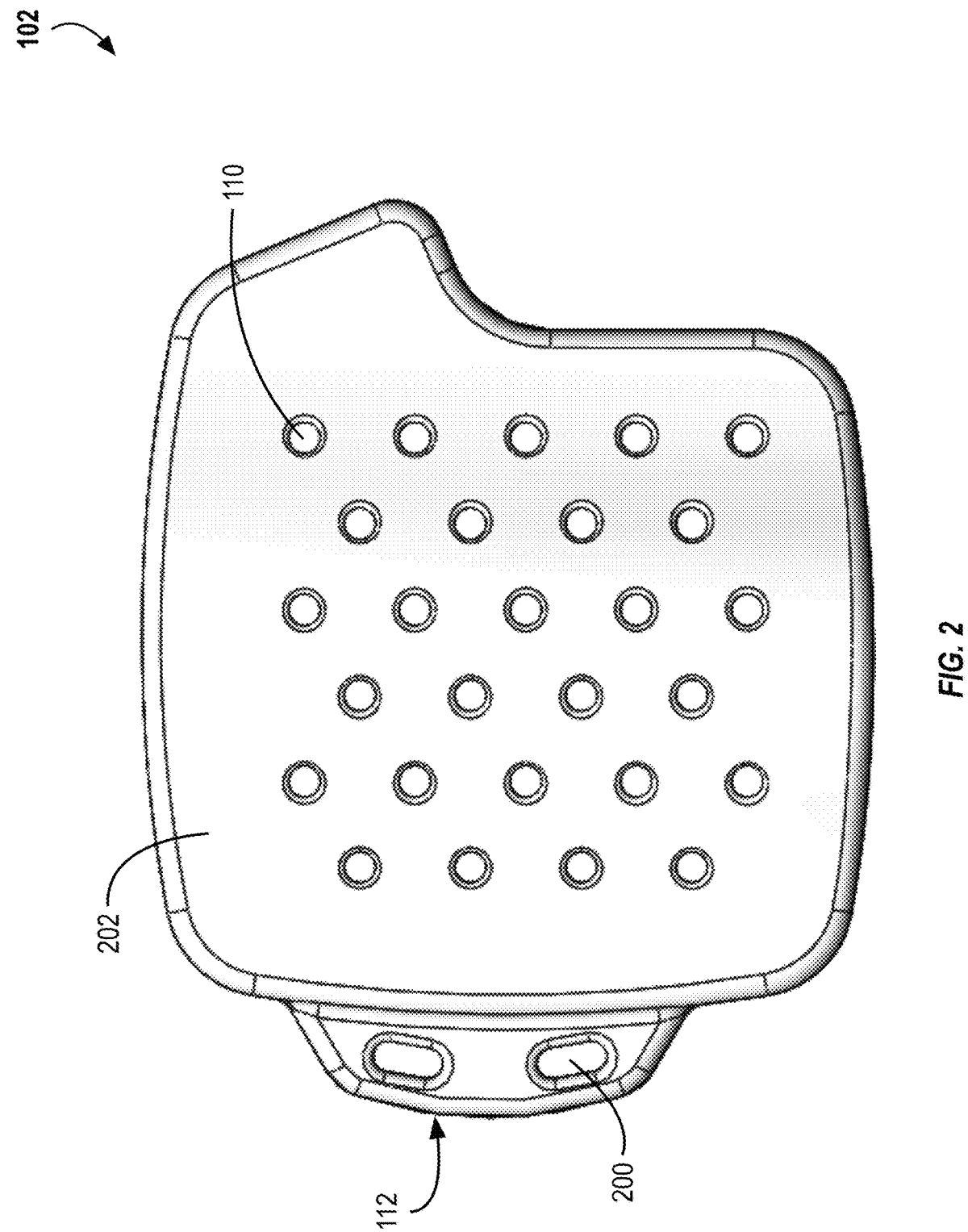
FIG. 2 illustrates a front view of the housing illustrated in FIG. 1.
Figure 3:
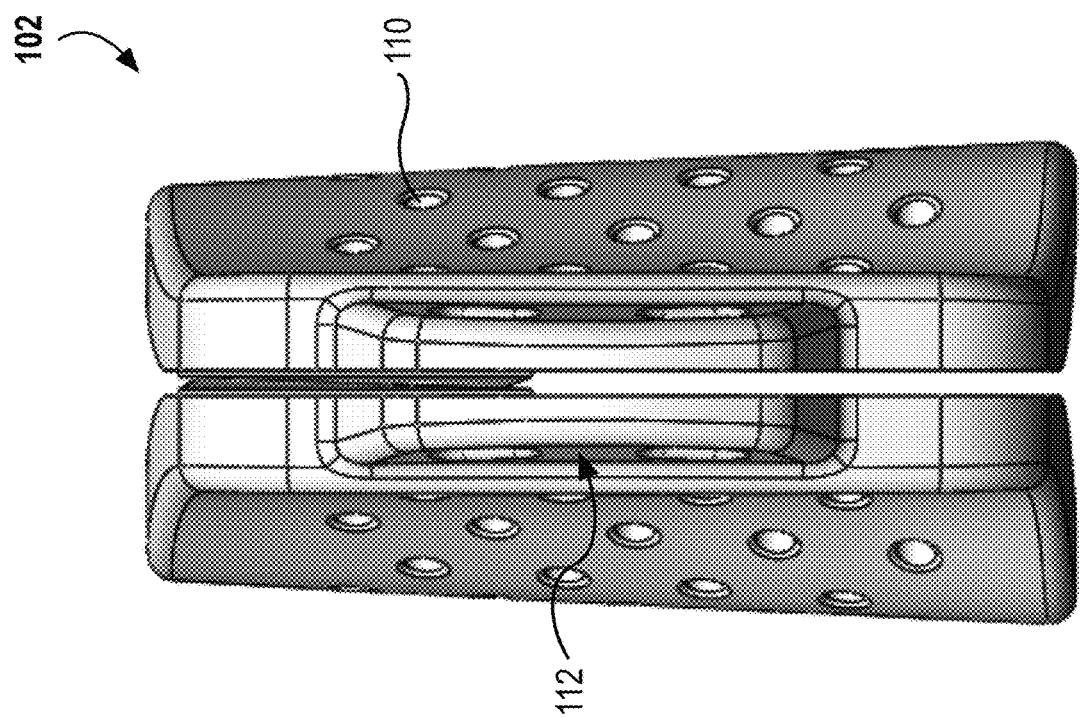
FIG. 3 illustrates a side view of the housing illustrated in FIG. 1.
Figure 4:
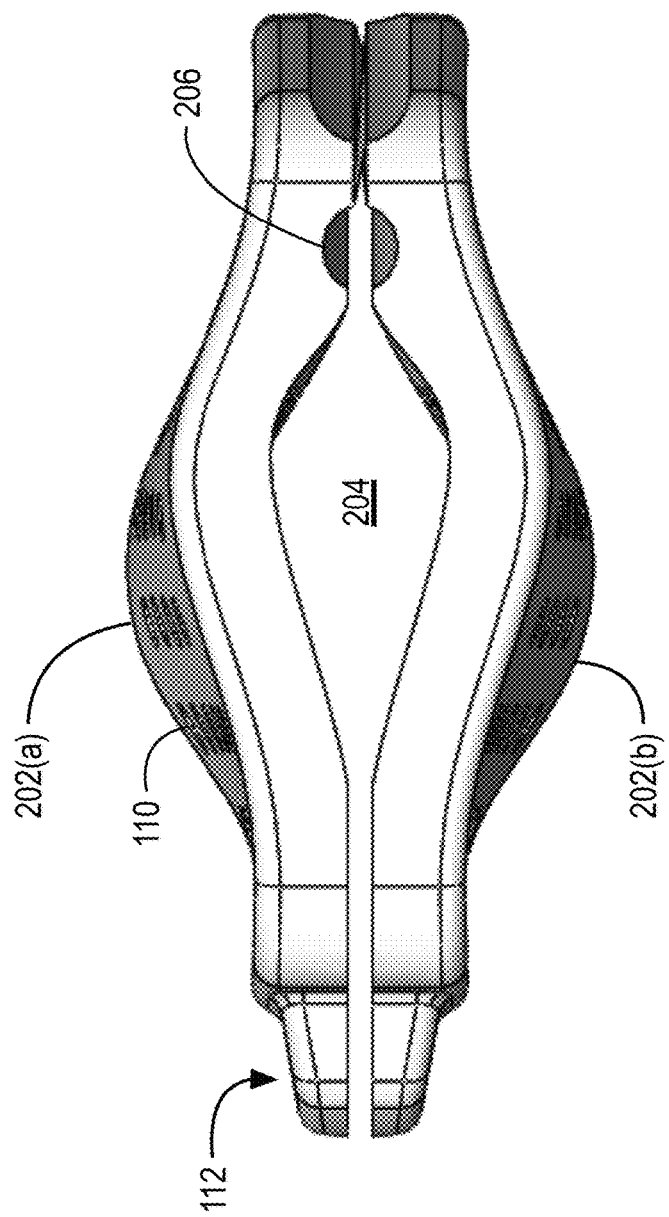
FIG. 4 illustrates a top view of the housing illustrated in FIG. 1.
Figure 5:
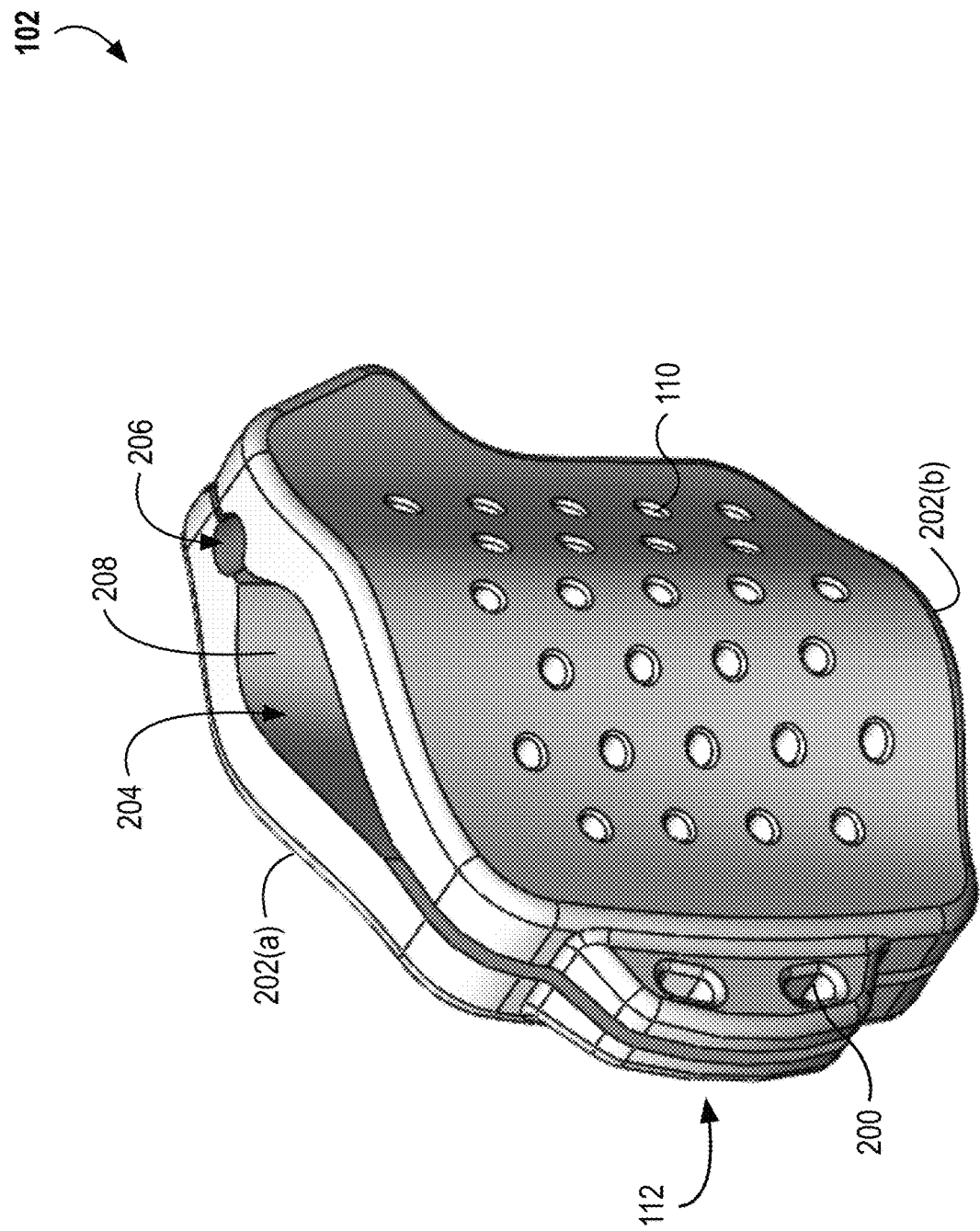
FIG. 5 illustrates a perspective view of the housing illustrated in FIG. 1 in a closed state.
Figure 6:
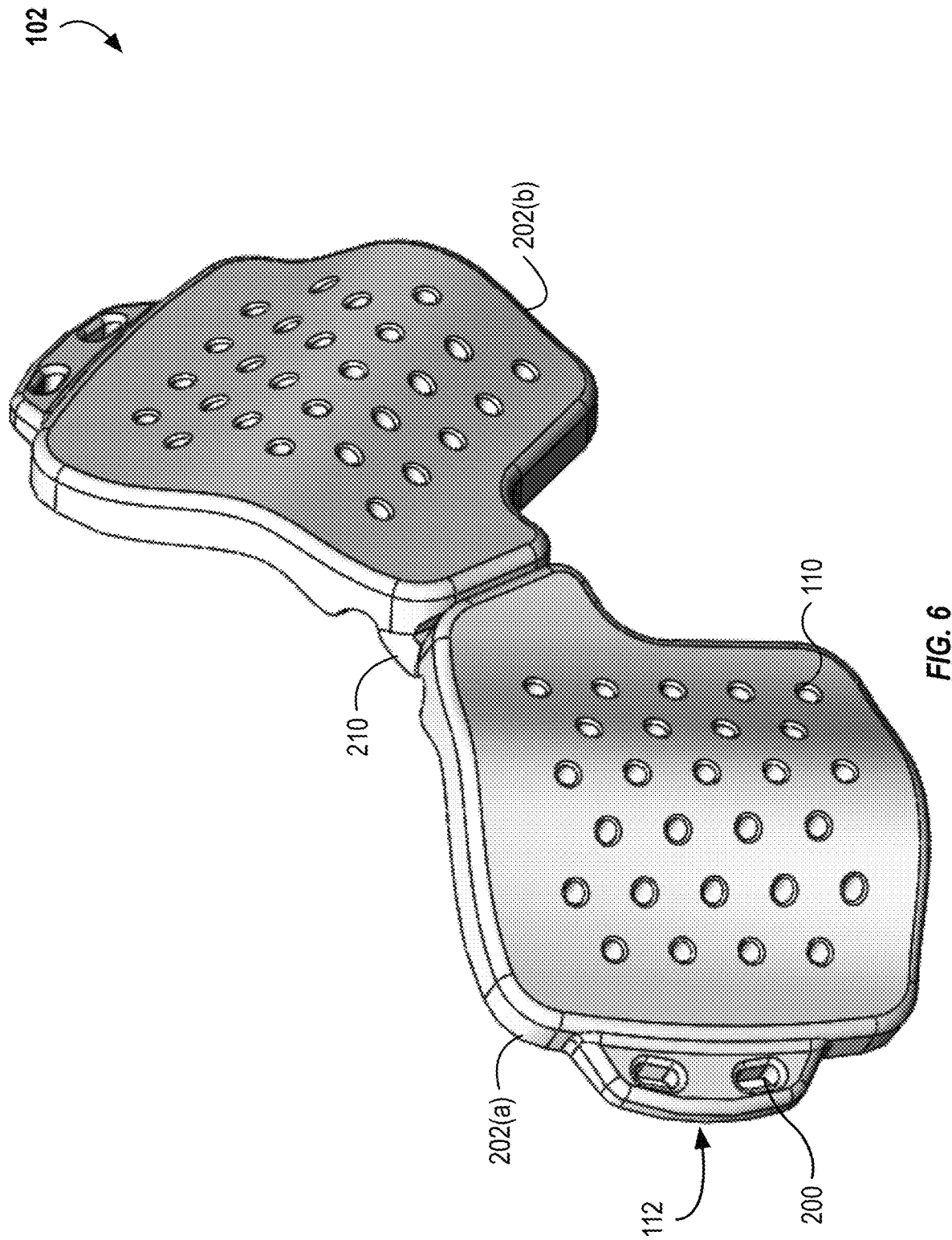
FIG. 6 illustrates a perspective view of the housing illustrated in FIG. 1 in an open state.

FIG. 2 illustrates a front view of the housing 102. FIG. 3 illustrates a side view of the housing 102. FIG. 4 illustrates a top view of the housing 102. FIG. 5 illustrates a perspective view of the housing 102 in a closed state. FIG. 6 illustrates a perspective view of the housing 102 in an open state. The housing 102 is configured to secure the mesh film 104 to the tissue, such that the mesh film's electrodes make electrical contact with the tissue. For example, the housing 102 can open and then closed around a target site. The electrodes can line one or more inner faces of the housing 102 such that when the housing 102 is closed around the target tissue the housing 102 brings the electrodes into contract with the target tissue. The housing 102 can be secured or anchored to another tissue other than the target tissue with which it is in electrical contact. For example, if the target tissue of the electrode contact is the carotid artery, the housing 102 can be secured to a different anatomy such as the C3 vertebra.

Referring to FIGS. 2-6, among others, the housing 102 includes a first side plate 202(a) and a second side plate 202(b), which are collectively referred to as side plates 202. The side plates 202 include a plurality of holes 110. Each side plate 202 also includes a fastening 112. The fastenings 112 can include holes 200.

The side plates 202 can be pliable or soft. For example, the side plates 202 can include a medical-grade silicone or plastic material or metal. In some implementations, the side plates 202 can include an internal support structure coated with a medical-grade silicone or plastic. For example, the side plates 202 can include an internal, stainless-steel or firm plastic support structure that can provide shape and support to the side plates 202. The support structure can be coated with the medical-grade silicone or plastic. In some implementations, the side plate 202 can be formed as a solid medical-grade silicone or plastic. The side plates 202 can be formed through an injection molding process, for example.

The side plates 202 can include a plurality of holes 110. The holes 110 can pass from an outer face of a side plate 202 to the side plate's inner face. For example, the holes 110 can pass through the body of each side plate 202. The holes 110 can enable nutrition, fluids, and gasses to pass through the housing 102 to the tissue (e.g., the artery) positioned within the housing 102. The holes 110 can have a diameter between about 0.2 mm and about 5 mm, between about 0.2 mm and about 3 mm, or between about 0.2 mm and about 2 mm.

Each of the side plates 202 can include a bow that enables an opening 204 to be formed between the first side plate 202(a) and the second side plate 202(b) when the first side plate 202(a) and the second side plate 202(b) are in their closed positions. The opening 204 provides a space for tissue (e.g., the carotid artery) to pass between the side plates 202. The bow and opening 204 are configured such that the tissue passing between the side plates 202 comes into contact with the nerve cuff 100 without substantially impacting blood flow through the tissue. The opening 204, at its widest location, can be between about 2 mm and about 9 mm, between about 4 mm and about 8 mm, or between about 4.5 mm and about 7 mm when targeting the carotid artery. When targeting different anatomies, the opening 204, at its widest location can be sizes proportionally to the anatomy. In some implementations, the side plates 202 do not include the bow when not deployed. For example, the side plates 202 are manufactured as substantially planer. The side plates 202 can be substantially compliant such that the side plates 202 can wrap or deform around the tissue passing through the nerve cuff 100. For example, the sides can include a metal-based core coated in silicone. A surgeon, when placing the nerve cuff 100, can bend or deform one or more of the side plates 202 (e.g., the metal-based core) and the side plates 202 can retain the bent or deformed shape. The surgeon can bend or deform the side plates 202 to conform to the shape of the target tissue.

The side plates 202 can each include an inner face 208. The mesh film 104 can be coupled with the inner faces 208. For example, the mesh film 104 can be coupled with the inner faces 208 with an epoxy. In some implementations, the mesh film 104 can be coupled with the inner faces 208 by partially embedding the mesh film 104 within the side plates 202. For example, the mesh film 104 can be positioned into a mold and the material of the side plates 202 can then be injected into the mold to form the side plates 202 with the mesh film 104 partially embedded within the side plates 202. The inner faces 208 can include one or more landmarks or registration marks that enable the mesh film 104 to be correctly positioned and aligned within the housing 102. For example, the inner faces 208 can include one or more registration posts. The mesh film 104 can include a plurality of registration holes that can be positioned over each of the registration posts to align the mesh film 104 within the housing 102.

The side plates 202, when in their closed position, can define a slot 206. For example, each side plate 202 can include an indentation or groove on their respective inner faces 208. When the side plates 202 are closed, the grooves can align to form the slot 206. The slot 206 can be a void in which a bridge of the mesh film 104 can form a fold with a radius of about 0.20 mm. The radius can be between about 0.10 mm and about 1.5 mm, between about 0.10 mm and about 1 mm, or between about 0.2 mm and 0.5 mm. For example, the slot 206 can enable the bridge to fold without forming a crease in the bridge.

The housing 102 can include a fastening 112. The fastening 112 can be used to close and secure the side plates 202 together. The fastening 112 can be positioned on a side of the housing 102 opposite the hinge 210. The hinge 210 can be a living hinge. The housing 102 can include a plurality of fastenings 112. For example, the housing 102 can include a first fastening 112 on a first side of the housing 102 that is positioned toward the top of the first side and a second fastening 112 on the first side of the housing 102 that is positioned toward the bottom of the first side.

The fastening 112 can include one or more holes 200. When closed, the fastening's holes 200 on the first side plate 202(a) can align with the fastening's holes 200 on the second side plate 202(b). After implantation, a surgeon can secure the side plates 202 into a closed position by passing a suture through the fastenings' holes 200 and suturing the two fastenings 112 together. The fastenings 112 can include other forms of fasteners, clips, or clasps to secure the first side plate 202(a) and the second side plate 202(b) together. For example, the housing 102 can be component of a kit that also includes a clip. The clip can be used to secure the first fastening 112 to the second fastening 112.

The housing 102 can include a hinge 210 that can couple the first side plate 202(a) with the second side plate 202(b). The hinge 210 can enable an angle of rotation between the first side plate 202(a) and the second side plate 202(b). The hinge 210 can enable the side plates 202 to be temporally separated to enable the nerve cuff 100 to be wrapped around the target tissue. For example, the never cuff 100 can be opened via the hinge 210 to expose the opening 204. The surgeon can place the target tissue within the opening 204 and close the nerve cuff 100.

Figure 7:
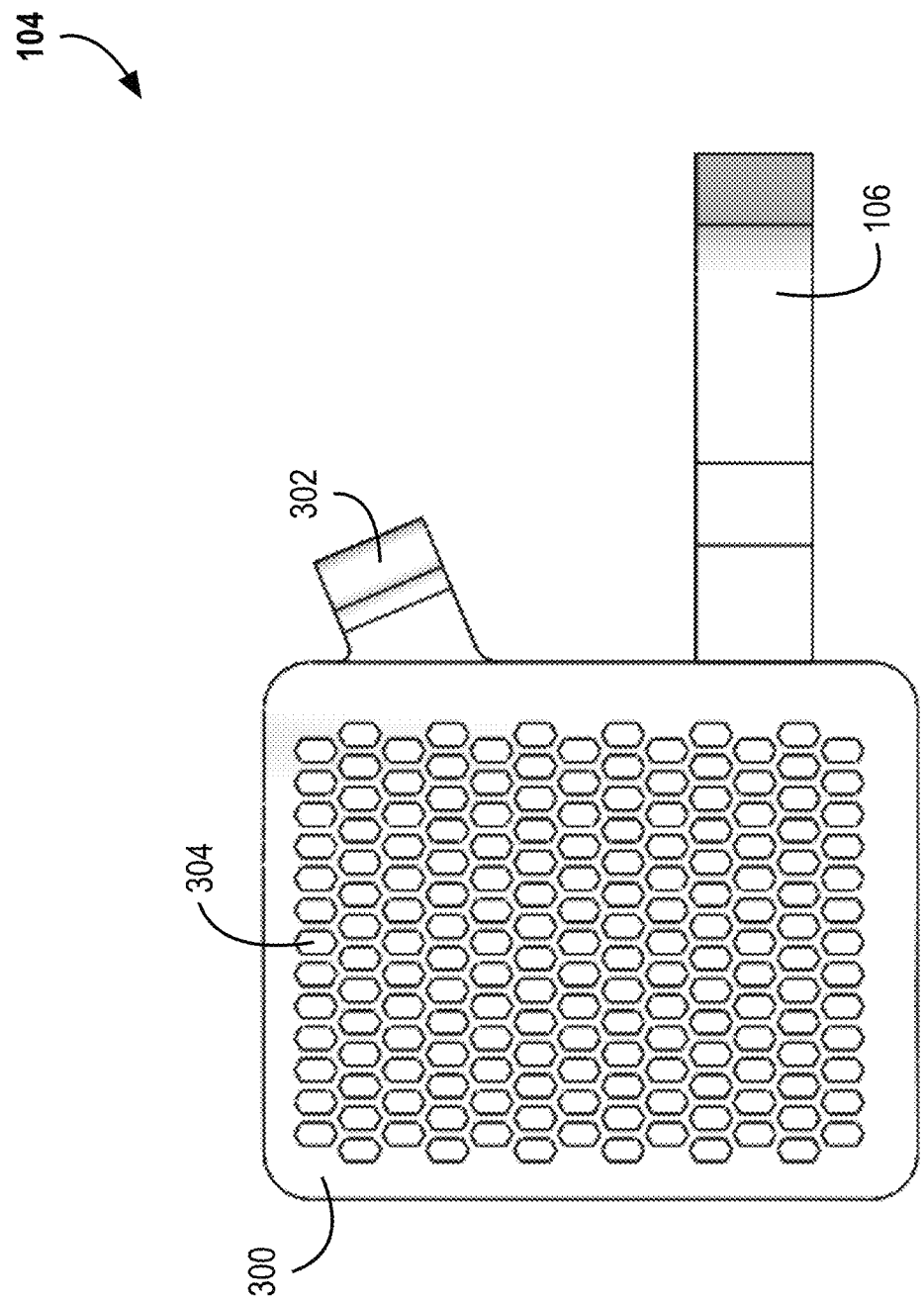
FIG. 7 illustrates a front view of the mesh film, which can be used in the nerve cuff illustrated in FIG. 1.
Figure 8:
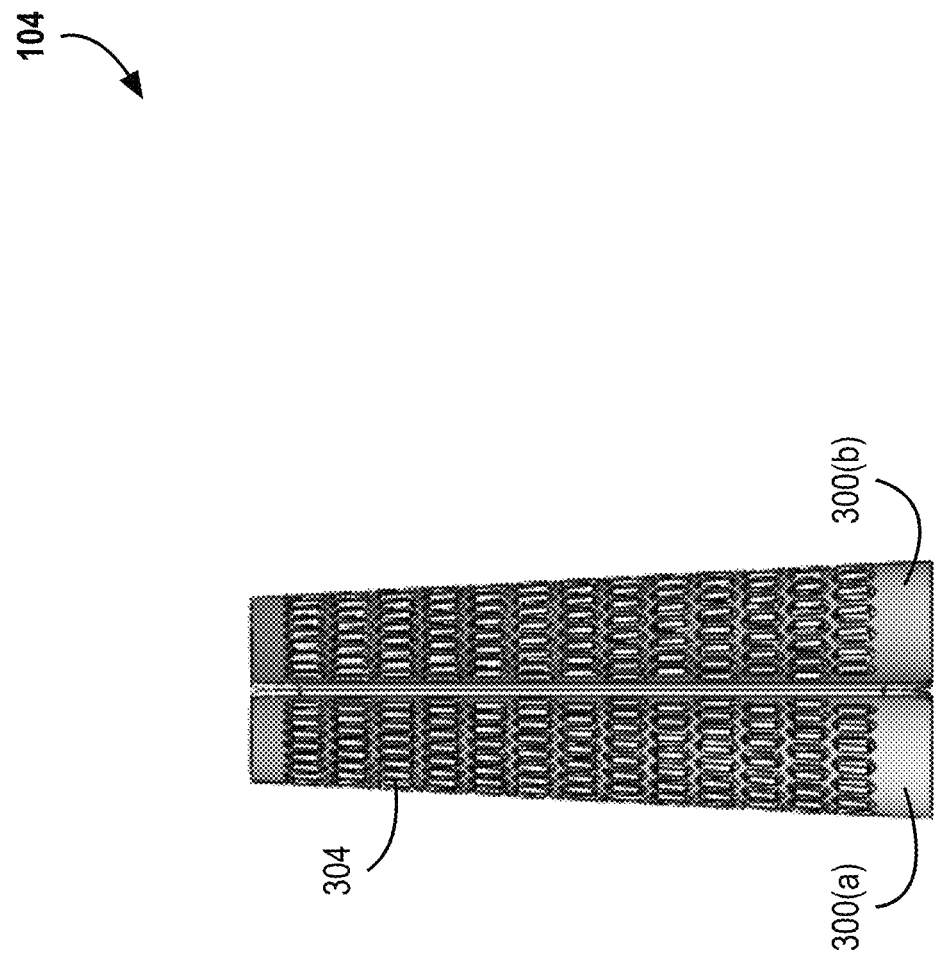
FIG. 8 illustrates a side view of the mesh film, which can be used in the nerve cuff illustrated in FIG. 1.
Figure 9:
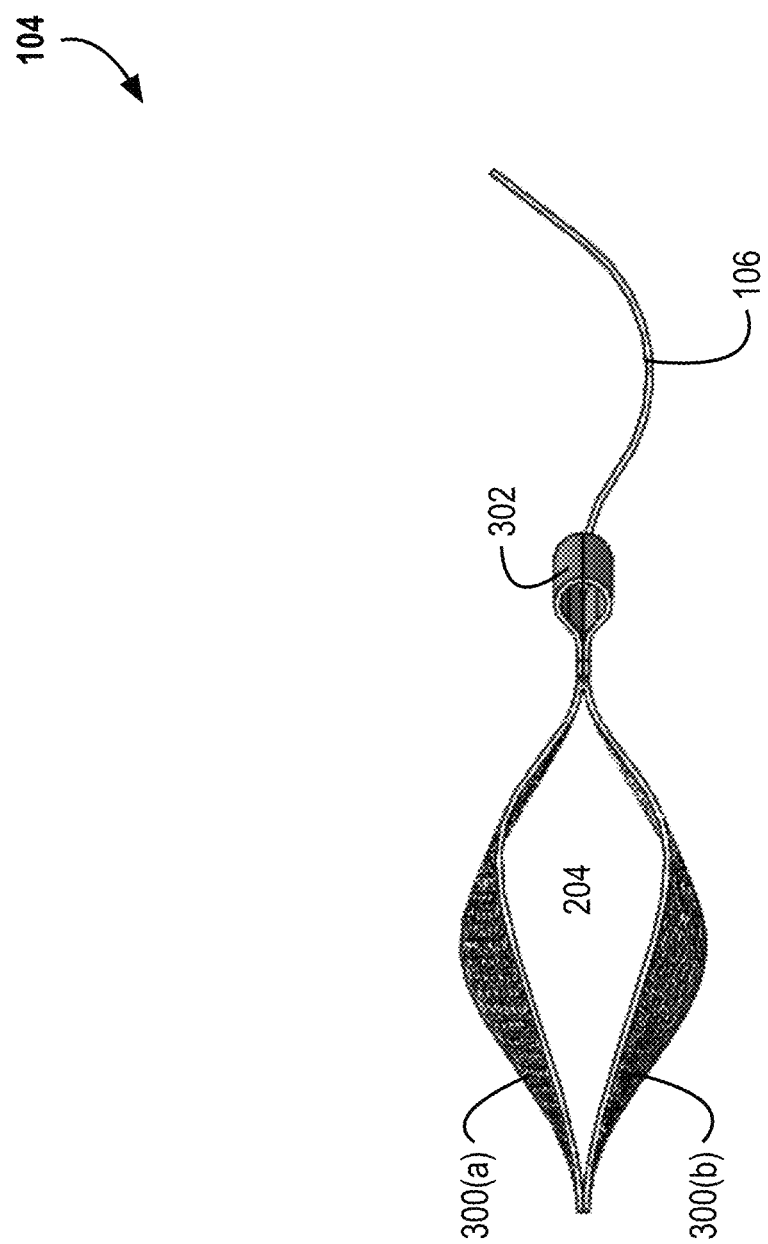
FIG. 9 illustrates a top view of the mesh film, which can be used in the nerve cuff illustrated in FIG. 1.
Figure 10:
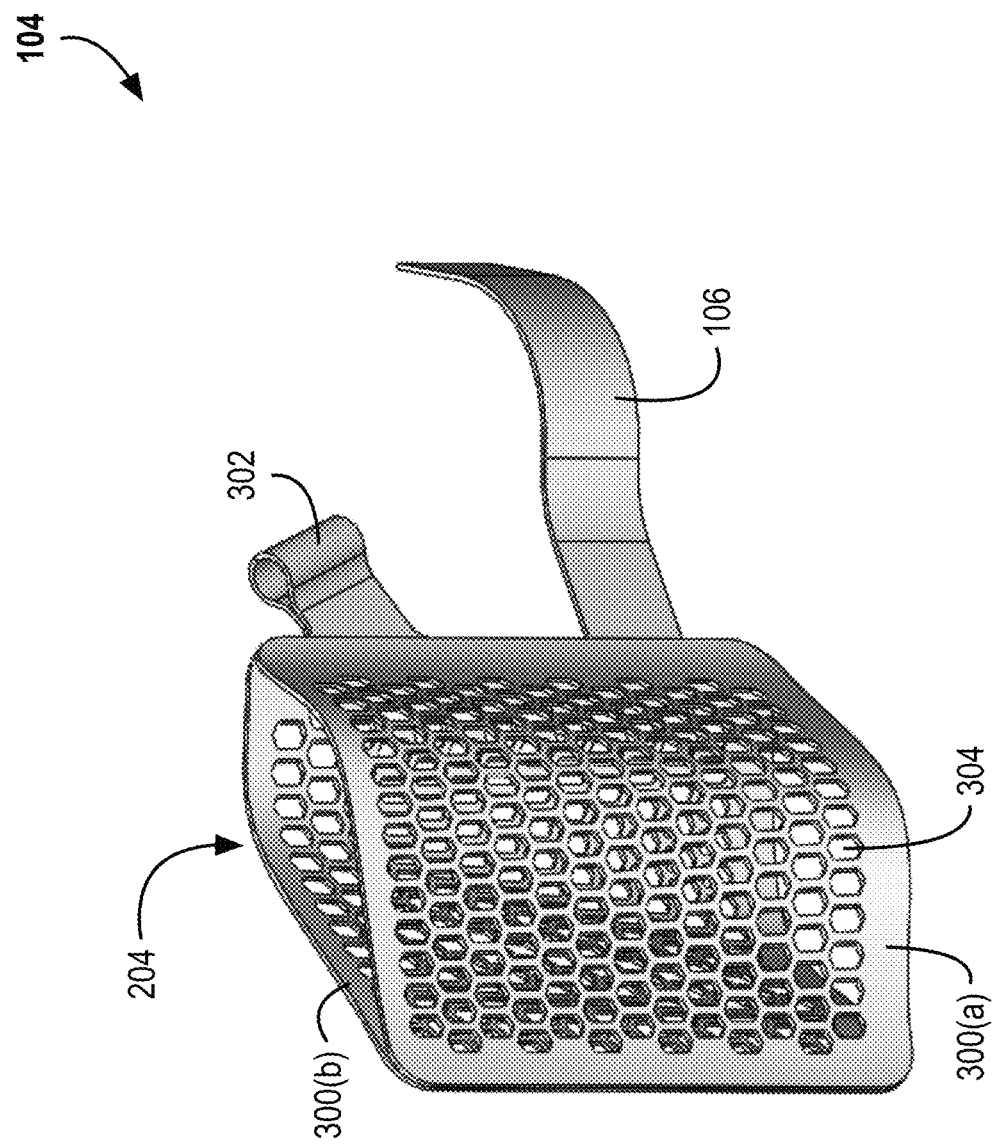
FIG. 10 illustrates a perspective view of the mesh film, which can be used in the nerve cuff illustrated in FIG. 1.
Figure 11:
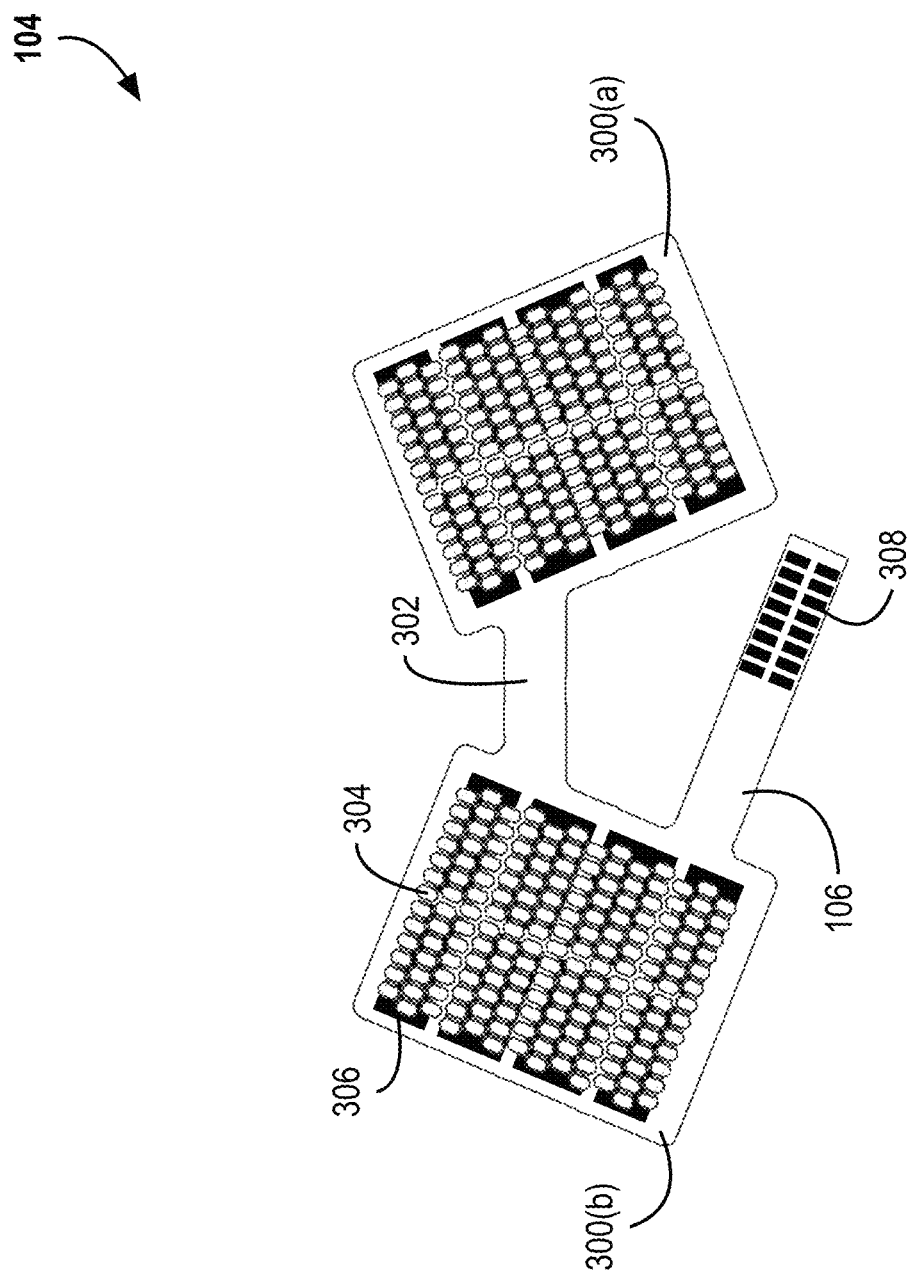
FIG. 11 illustrates a planar view of the mesh film, which can be used in the nerve cuff illustrated in FIG. 1.

FIG. 7 illustrates a front view of the mesh film 104 in a closed state. FIG. 8 illustrates a side view of the mesh film 104. FIG. 9 illustrates a top view of the mesh film 104. FIG. 10 illustrates a perspective view of the mesh film 104. FIG. 11 illustrates a planar view of the mesh film 104. The mesh film 104 can be coupled to the inner faces 208 of the housing 102.

The orientation of the mesh film 104 illustrated in FIG. 7 can correspond to the orientation of the housing in FIG. 2. For example, FIG. 7 illustrates the orientation and view of the mesh film 104 as if the mesh film 104 is coupled with the inner faces 208 of the housing 102 and the housing 102 is orientated as illustrated in FIG. 2. The orientation of the mesh film 104 illustrated in FIG. 8 can correspond to the orientation of the housing in FIG. 3. The orientation of the mesh film 104 illustrated in FIG. 9 can correspond to the orientation of the housing in FIG. 4. The orientation of the mesh film 104 illustrated in FIG. 10 can correspond to the orientation of the housing in FIG. 5.

Referring to FIGS. 7-11, among others, the mesh film 104 can be a MEMS film. The mesh film 104 can include a thin-film elastic mesh with an integrated array of electrodes 306. The mesh film 104 includes a first panel 300(a) and a second panel 300(b), which can collectively be referred to as the panels 300. The panels 300 includes a plurality of openings 304. The first panel 300(a) can be coupled with the second panel 300(b) via a bridge 302. The mesh film 104 can be coupled with an external source, such as an implantable pulse generator, via the tether 106. The tether 106 can extend from one of the panels 300.

The mesh film 104 can be formed as a planer MEMS film. The mesh film 104 can include a plurality of layers. For example, the mesh film 104 can include one or more metal layers. The electrodes 306 can be defined in the one or more metal layers. Electrical traces that couple the electrodes 306 to the contacts 308 on the tether 106 can also be defined in the metal layers. The metal layers can also include vias that couple different metal layers together. The metal layers can include platinum, iridium oxide, titanium, or any combination thereof. The metal layer can be deposited onto a barrier layer and etched to form the traces, contacts, and electrodes of the metal layers.

The mesh film 104 can include a plurality of barrier layers. For example, the barrier layers can be silicon-based barrier layers that insulate the metal layers from one another or from an external environment. The mesh film 104 can include one or more barrier layers that encapsulate at least a portion of the mesh film 104. For example, the barrier layers can be polyimide layers that encapsulate the metal and silicon-based layers. Portions of the barrier layer covering the electrodes 306 can be removed to expose the electrodes 306 to the external environment. For example, the portions of the barrier layer covering the electrodes 306 can be removed with a chemical etch or laser micromachining.

The mesh film 104 can include the first panel 300(a) and the second panel 300(b). The panels 300 can be about 12 mm width by about 20 mm high. For example, the panels 300 can have a width between about 5 mm and about 30 mm, between about 5 mm and about 25 mm, or between about 10 mm and about 20 mm, and the panels 300 can have a height between about 10 mm and about 50 mm, between about 10 mm and about 40 mm, or between about 15 mm and about 25 mm. The electrodes 306 can be positioned on the inner face of the panels 300. Each panel 300 can include between about 2 and about 32, between about 2 and about 28, between about 4 and about 16, between about 4 and about 12, between about 8 and about 12, between about 8 and about 16, between about 8 and about 24, or between about 8 and 32 electrodes 306. For example, as illustrated, each panel 300 includes 8 electrodes 306. The first panel 300(a) and the second panel 300(b) can include the same number of electrodes 306 or the first panel 300(a) and the second panel 300(b) can include a different number of electrodes 306. The electrodes 306 can be individually addressable. For example, each of the electrodes 306 can be coupled to a respective contact 308. The electrodes 306 can be addressed as a group. For example, two or more electrodes 306 can be coupled to the same contact 308.

The panels 300 can include a plurality of openings 304. The openings 304 can facilitate the expansion and contraction of the mesh film 104 without applying detrimental pressure to tissue passing through the nerve cuff 100. The openings 304 can be Y-shaped openings, circular openings, rectangular openings, square openings, or any other geometric shape, or combination of shapes. In some implementations, the openings 304 can be a series of parallel slits through the panel 300. The openings 304 can have a size between of about 0.2 mm wide and about 0.35 mm high. For example, the openings 304 can have a width between about 0.05 mm and about 2 mm, between about 0.1 mm and about 1 mm, or between about 0.1 mm and about 0.5 mm, and the openings 304 can have a height between about 0.1 mm and about 3 mm, between about 0.1 mm and about 2 mm, or between about 0.1 mm and about 1 mm.

The first panel 300(a) can be coupled with the second panel 300(b) via the bridge 302. The bridge 302 can include the electrical traces that travel from the contacts 308 to the electrodes 306 that are positioned on the first panel 300(a). When in the closed position, the bridge 302 can fold upon itself. The slot 206 enables the bridge 302 to fold upon itself with a bend radius of about 0.2 mm.

Figure 12:
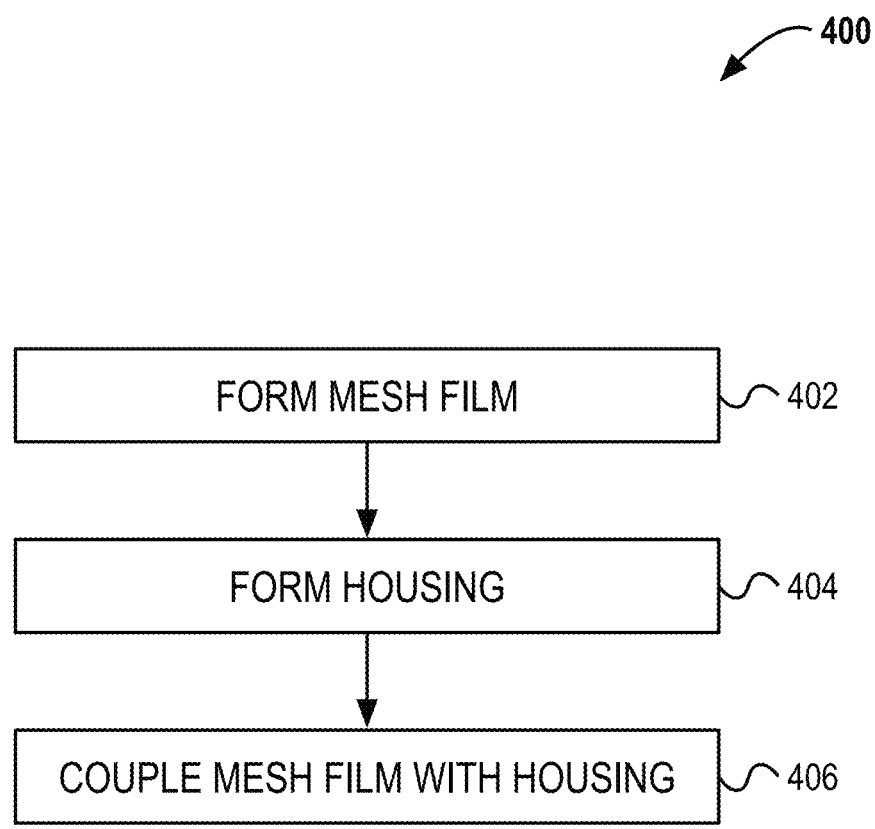
FIG. 12 illustrated a block diagram of an example method to manufacture the nerve cuff illustrated in FIG. 1.

FIG. 12 illustrated a block diagram of an example method 400 to manufacture the nerve cuff. The method 400 can include forming the mesh film (ACT 402). The method 400 can include forming the housing (ACT 404). The method 400 can include coupling the mesh film with the housing (ACT 406).

As set forth above, the method 400 can include forming a mesh film. The fabrication procedure of the mesh film can include a series of procedural steps in which various layers are deposited or removed (e.g., etched) to achieve a final form. For example, a carrier substrate can be provided, such as a wafer composed of a crystalline material, such as silicon, or an amorphous material, such as a thermal shock resistant borosilicate glass or other suitable smooth supportive material. One or more sacrificial layers can be deposited on the wafer.

A first polymeric layer can be deposited on the sacrificial layer. The first polymeric layer can be deposited upon the sacrificial layer by MEMS processes such as, but not limited to, (i) spin coating a liquid polymer precursor such as Polyimide or Silicone precursor; (ii) depositing a polymer through chemical vapor deposition as is done with parylene-C; or (iii) laminating a polymer sheet onto the wafer. Once deposited the first polymeric layer can be heated, or baked, to polymerize the first polymeric layer. The first polymer layer can form a barrier layer of the mesh film from water, humidity, fluids, and other components of the mesh film 104.

A silicon layer can then be deposited onto the first polymeric layer. The silicon based barrier layer can serve both as a layer to aid the adhesion and durability of subsequent layers. The silicon based barrier layer can also serve as an ionic barrier, and limit ions from reaching the metal layers, which could compromise electrical performance.

A metal layer can then be deposited over the silicon layer. Subsequently, a photoresist layer can be deposited onto the metal layer. The photoresist is defined to selectively expose portions of the metal layer. The exposed portions of the metal layer can be removed to define the electrodes, electrical traces, and contacts. Portions of the metal layer can be removed with a plasma etcher such as a Reactive Ion Etcher.

Additional silicon and barrier layers can be deposited to electrically isolate the components of the metal layer. The process can be repeated to add additional metal layers into the mesh film. Photoresists and/or micromachining can be used to remove portions of the silicon and barrier layers that are deposited over the metal layer to expose the electrodes and contacts. The sacrificial layer can be etched or dissolved to separate the formed mesh film from the wafer. The openings in the mesh film can be formed through micromachining or by die cutting the holes into the panels of the mesh film. In some implementations, the holes can be formed during the manufacture of the mesh film. For example, resists can be used to prevent the above described deposition steps from depositing material in the areas that will define the holes in the mesh film.

Referring to FIG. 12, the method 400 can include forming the housing (ACT 404). The housing can be manufactured through an injection molding process. For example, the housing's material can be heated, liquefied, and pumped into a mold that defines a negative of the housing. Once the material solidifies, the housing can be ejected from the mold.

The method 400 can include coupling the mesh film with the housing (ACT 406). In some implementations, the mesh film can be formed with registration marks. For example, the mesh film can include holes or notches that can align with posts formed on the inner faces of the housing. In some implementations, the mesh film can be coupled with the housing with a medical adhesive or epoxy. The inner faces of the housing can include small channels or grooves. When the mesh film is positioned against the inner faces of the housing, medical adhesive can be applied to the ends of the channels and, via capillary action, the glue can flow through the channels and beneath the mesh film to couple the mesh film and the housing together. The mesh film can be coupled with the housing through an over molding process. For example, the mesh film can be formed and placed in an injection molding mold. The housing can be injection molded around at least a portion of the mesh film to encapsulate or otherwise couple at least a portion of the mesh film with the housing.

The device described herein can benefit a variety of patient disease states. The device can be connected to an implantable stimulator. The implantable stimulator can generate electrical signals that can be transmitted the electrodes. For example, when applied to the carotid artery, the surface of which contains nerve bundles, the electrical stimulation to this anatomy may change certain cardiovascular states such as hypertension or provide vasodilation. As another example, when applied to the Vagus Nerve, the electrical stimulation to this anatomy may provide alleviation of epileptic seizures or depressive states. As another example, when applied to the Hypoglossal Nerve, the electrical stimulation to this anatomy may provide improvements in airway access during sleep. For example, the nerve cuff can be implanted and coupled around a target tissue to deliver electrical stimulation to and record from the target tissue. The target tissue can include one or more of a hypoglossal nerve, a vagus nerve, a carotid artery bundle, a carotid artery bundle, or a glossopharyngeal nerve.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including," "comprising," "having," "containing," "involving," "characterized by," "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. A reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

The invention claimed is:

1. An implantable cuff, comprising:
   a housing to at least partially enclose around a target tissue, the housing comprising:
      a first side plate having an inner face;
      a second side plate having an inner face, the second side plate coupled with the first side plate at a hinge to define an opening between the inner face of the first side plate and the inner face of the second side plate; and
      a plurality of registration marks on the inner face of the first side plate and the inner face of the second side plate; and
   a mesh film positioned within the opening defined by the first side plate and the second side plate of the housing and at least partially aligned with the plurality of registration marks, the mesh film comprising:
      a first panel coupled with the inner face of the first side plate via the plurality of registration marks to secure the mesh film to a set position around the target tissue within the housing, the first panel comprising a first plurality of electrodes;
      a second panel coupled with the inner face of the second side plate via the plurality of registration marks to secure the mesh film to the set position around the target tissue within the housing, the second panel comprising a second plurality of electrodes; and
      a bridge coupling the first panel with the second panel to electrically couple the first plurality of the electrodes on the first panel with the second plurality of electrodes on the second panel.

2. The implantable cuff of claim 1, the housing comprising:
   a first plurality of holes defined through the first side plate to enable at least one of a gas flow or a fluid flow through the first side plate; and
   a second plurality of holes defined through the second side plate to enable at least one of the gas flow or the fluid flow through the second side plate.

3. The implantable cuff of claim 1, the mesh film comprising:
   a first plurality of openings defined through the first panel; and
   a second plurality of openings defined through the second panel.

4. The implantable cuff of claim 1, comprising:
   a tether that extends from the first panel, the tether comprising a plurality of contacts.

5. The implantable cuff of claim 1, comprising:
   a tether that extends from the first panel, the tether comprising a plurality of contacts; and
   a plurality of traces, each of the plurality of traces couple one of the plurality of contacts to at least one first plurality of electrodes or second plurality of electrodes.

6. The implantable cuff of claim 1, comprising:
   a tether comprising a planar film extending from the first panel; and a plurality of traces, each of the plurality of traces defined on a metal layer in the planar film of the tether, the metal layer to electrically couple the first plurality of electrodes and the second plurality of electrodes with an external source.

7. The implantable cuff of claim 1, wherein the first side plate and the second side plate comprise a medical-grade silicone.

8. The implantable cuff of claim 1, the mesh film comprising:
   at least one metal layer that defines the first plurality of electrodes and the second plurality of electrodes; and
   at least one barrier layer that at least partially encapsulates the at least one metal layer.

9. The implantable cuff of claim 1, wherein the target tissue is one of a hypoglossal nerve, a vagus nerve, a carotid artery bundle, or a glossopharyngeal nerve.

10. A method, comprising:
    forming a film to contact with a target tissue, the film comprising:
      a first panel comprising a first plurality of electrodes;
      a second panel comprising a second plurality of electrodes; and
      a bridge coupling the first panel with the second panel to electrically couple the first plurality of the electrodes on the first panel with the second plurality of electrodes on the second panel;
    forming a housing to at least partially enclose around the target tissue comprising:
      a first side plate having an inner face;
      a second side plate having an inner face, the second side plate coupled with the first side plate at a hinge to define an opening between the inner face of the first side plate and the inner face of the second side plate; and
      a plurality of registration marks on the inner face of the first side plate and the inner face of the second side plate; and
    positioning the film within the opening defined by the first side plate and the second side plate of the housing; and
    coupling the first panel of the film with the inner face of the first side plate and the second panel of the film with the inner face of the second side plate via the plurality of registration marks on the inner face of the first side plate and the inner face of the second side plate to secure the film about the target tissue to a set position within the housing.

11. The method of claim 10, comprising:
    forming a first plurality of holes through the first side plate to enable at least one of a gas flow or a fluid flow through the first side plate; and
    forming a second plurality of holes through the second side plate to enable at least one of the gas flow or the fluid flow through the second side plate.

12. The method of claim 10, comprising:
    defining a first plurality of openings through the first panel; and
    defining a second plurality of openings through the second panel.

13. The method of claim 10, comprising:
    forming a tether extending from the first panel, the tether comprising a plurality of contacts.

14. The method of claim 10, comprising:
    forming a tether extending from the first panel, the tether comprising:
      a plurality of contacts; and
      a plurality of traces, each of the plurality of traces coupling one of the plurality of contacts to at least one first plurality of electrodes or second plurality of electrodes.

15. The method of claim 10, comprising:
    forming a tether comprising a planar film extending from the first panel, the tether comprising:
      a plurality of traces, each of the plurality of traces defined on a metal layer in the planar film of the tether, the metal layer to electrically couple the first plurality of electrodes and the second plurality of electrodes with an external source.

16. The method of claim 10, comprising forming the first side plate and the second side plate by injection molding a medical-grade silicone.

17. The method of claim 10, comprising:
    etching at least one metal layer defining the first plurality of electrodes and the second plurality of electrodes; and
    at least partially encapsulating the at least one metal layer with at least one barrier layer.

18. The method of claim 10, comprising:
    coupling the film with the housing with an epoxy.

19. The method of claim 10, comprising:
    deforming at least one of the first side plate and the second side plate to define an opening between the first side plate and the second side plate.

20. The implantable cuff of claim 1, wherein the first panel and the second panel of the mesh film having a width ranging between 5 mm and 30 mm and a height ranging between 10 mm and 50 mm.

* * * * *